United States Patent [19]
Strokon

[11] Patent Number: 5,192,321
[45] Date of Patent: Mar. 9, 1993

[54] APPARATUS AND METHOD FOR KNEE SURGERY

[76] Inventor: Andrew Strokon, 49 Renwick St., Leichhardt, New South Wales 2040, Australia

[21] Appl. No.: 499,884

[22] Filed: Mar. 27, 1990

[30] Foreign Application Priority Data

Mar. 29, 1989 [AU] Australia .............................. PJ3415

[51] Int. Cl.$^5$ .............................................. A61F 2/00
[52] U.S. Cl. .......................................... 623/13; 606/1; 606/88; 606/96
[58] Field of Search ............. 606/60, 73, 74, 79, 606/80, 83, 86, 87, 88, 95, 96, 104, 1; 623/43

[56] References Cited

U.S. PATENT DOCUMENTS

| | | | |
|---|---|---|---|
| 3,896,500 | 7/1975 | Rambert et al. | 623/13 |
| 4,257,411 | 3/1981 | Cho | 606/96 |
| 4,535,768 | 8/1985 | Hourahane et al. | 606/86 |
| 4,668,233 | 5/1987 | Seedhom et al. | 623/13 |
| 4,775,380 | 10/1988 | Seedhom et al. | 623/13 |
| 4,784,126 | 11/1988 | Hourahane | 606/60 |
| 4,828,562 | 5/1989 | Kenna | 623/13 |
| 4,834,752 | 5/1989 | Van Kampen | 623/13 |
| 4,865,025 | 9/1989 | Buzzi et al. | 606/96 |
| 4,881,537 | 11/1989 | Henning | 623/13 |
| 4,950,271 | 8/1990 | Lewis et al. | 623/13 |
| 4,973,332 | 11/1990 | Kummer | 606/73 |
| 5,042,983 | 8/1991 | Rayhack | 606/87 |

FOREIGN PATENT DOCUMENTS

| | | | |
|---|---|---|---|
| 0168885 | 9/1951 | Austria | 606/96 |
| 0095296 | 11/1983 | European Pat. Off. | 606/88 |
| 0250255 | 10/1987 | Fed. Rep. of Germany | 606/96 |
| 1223899 | 4/1986 | U.S.S.R. | 606/60 |

Primary Examiner—Stephen C. Pelegrino
Assistant Examiner—Glenn Dawson
Attorney, Agent, or Firm—Ladas & Parry

[57] ABSTRACT

A method of cruciate ligament replacement using a graft having a section of patellar tendon and sections of its boney attachment at either end harvested with an apparatus having a dowel cutter and a mounting device for the dowel cutter, the mounting device having an arm rigidly interconnected with means for rotatably mounting the dowel cutter, the arm extending to a remote location at which it is adapted to be secured, e.g. by pins, to boney structure located beneath the arm. A second apparatus is used to permit accurate guiding of fixing pins through a tibia or femur and comprises a rigid track and a cylindrical stem at right angles to the track and adapted to be inserted in a drilled canal in the bone. A sliding block on the track has bores at right angles to the stem to accommodate the fixing pin which, in a first step of the operation, can be inserted through the bone to abut the stem before the apparatus is withdrawn so that the boney plug of the graft can be inserted in the canal and then the pin can be driven home to secure the boney plug in position.

4 Claims, 5 Drawing Sheets

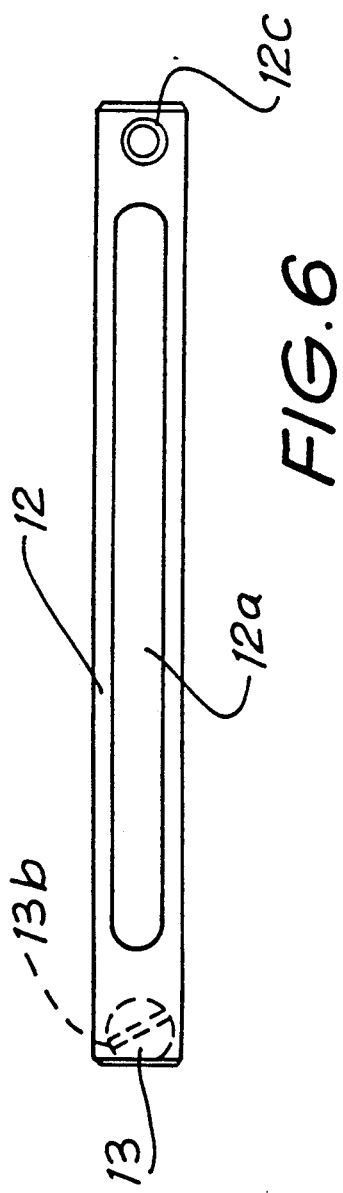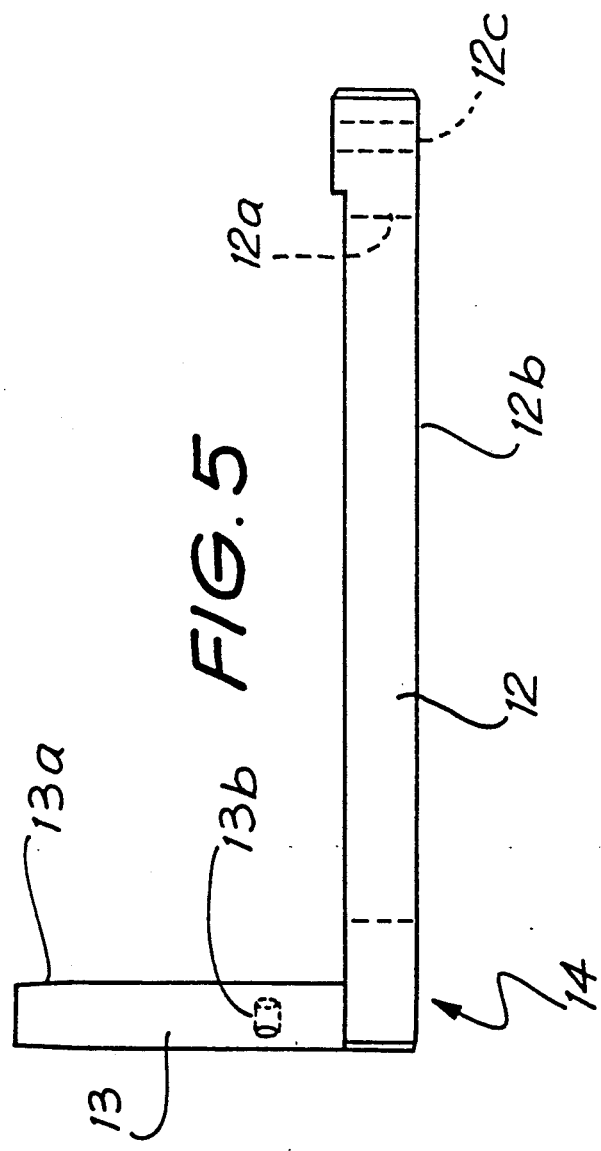

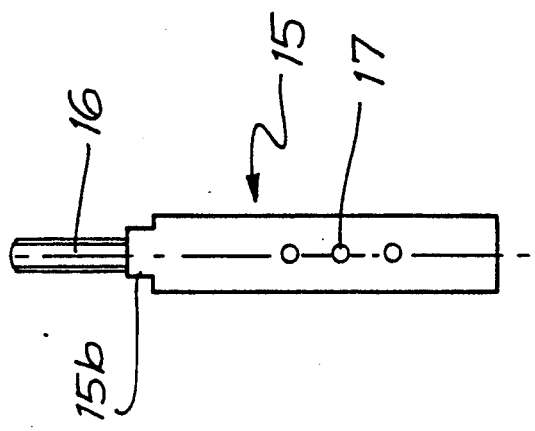
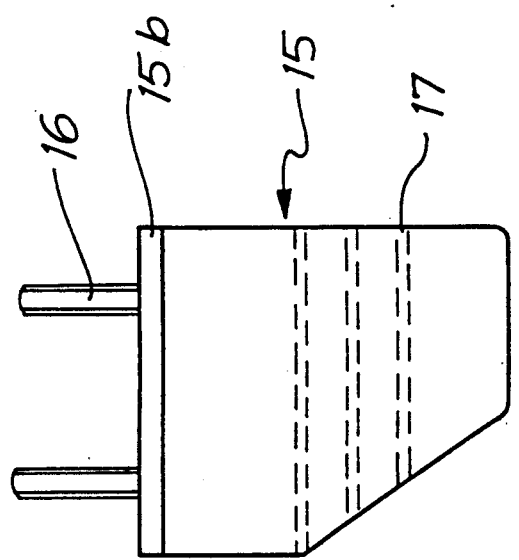

APPARATUS AND METHOD FOR KNEE SURGERY

FIELD OF THE INVENTION

The present invention relates to an apparatus and method for harvesting a graft comprising plugs of boney structure and contiguous tendon fibers and also to apparatus and a method for installing the graft in a joint.

BACKGROUND TO THE INVENTION

The present invention will be defined by reference to the Clancy method of knee surgery but it is to be understood that the operation or an analagous operation may be performed on similar joints on humans and on other animals.

The cruciate ligaments form the intra-articular ligaments that stretch between the tibia and femur. The cruciate ligaments are strong, rounded bands which cross each other between their attachments, and are distinguished as the anterior and posterior cruciate ligaments. The anterior cruciate ligament extends obliquely upwards and backwards from the non-articular area in front of the intercondylar notch of the tibia to the back part of the medial side of the lateral femoral condyle.

The cruciate ligaments are vulnerable to extensive damage. The ligaments are prone to "tearing" rendering them incapable of performing their normal function, and this frequently occurs as a result of a sporting injury. Consequently, the ligaments need to be surgically replaced so as to prevent antero-posterior displacement of the tibia and to limit medial rotation of the tibia and lateral rotation of the femur.

It has been found that a suitable replacement for the cruciate ligament is the patellar tendon. The patellar tendon has the following characteristics and properties which enable it to best perform the role of the cruciate ligament: the patellar tendon

- has excellent tensile strength;
- is easily accessible;
- is the proper length;
- remains viable since it can carry its own blood supply from the infrapatellar fat pad;
- both ends have a boney attachment to secure the graft.

Clancy and Associates have described a method of replacing a torn or damaged cruciate ligament with a patellar tendon. This method involves using a central strip of the patellar tendon based on a vascular pedicle from the infrapatellar fat pad. The success of the Clancy method depends on careful technical execution and precise placement of drill holes and a sound fixation of the contiguous bone blocks at each end of the graft. Previously, harvesting of the contiguous bone block was performed with power tools such as air driven saws and osteotomes to produce a strip of bone approximately 3 cm long 10 mm wide with a depth of 5 mm. The bone has on its flat surface the superficial fibers of the patellar tendon. This approximately triangular piece of bone is placed into a drilled tunnel in the femur and tibia respectively and fixed with sutures tied over a button placed at the mouth of the exiting tunnel.

There are disadvantages associated with the Clancy's procedure:

1. A triangular bone block fits poorly in the tunnel.
2. The fixation threads or button may break.
3. The bone block may break or patella may be fractured during havesting of the bone block leading to inferior fixation.
4. Incongruous fit of bone graft means there is a lesser chance of a good boney union in the tunnel graft interface.

The present invention is directed towards obviating some of the aforementioned problems associated with the Clancy procedure.

SUMMARY OF THE INVENTION

In a first aspect of the present invention there is provided an apparatus for harvesting plugs of boney structure and contiguous tendon fibres, the apparatus comprising:

(a) mounting means for rotatably mounting a shaft of a dowel cutter with a cutting head adjacent a shoulder portion of the boney structure and having guide means for guiding the dowel cutter for movement along an operating axis for harvesting a plug of boney structure extending from the shoulder thereof; and (b) an arm rigidly interconnected with the mounting means and extending to a securing location which is remote from the mounting means and spaced therefrom in a direction which is generally along the operating axis in the direction in which the dowel cutter moves when cutting the plug, the securing location being adjacent the operating axis and having means to permit the arm to be secured to boney structure disposed thereunder, whereby the apparatus can effectively control operation of the dowel cutter.

When the apparatus is secured to the boney structure by way of securing means such as pins or screws, and the dowel cutter is supported by the guide means, the dowel cutter can be advanced by attaching a drill to the shaft of the dowel cutter in order to harvest a contiguous bone block.

Preferably, the mounting means comprises an elongated body part with a bore along the operating axis to accommodate the cutter with a sliding fit.

Preferably, the apparatus also includes auxiliary securing means being laterally offset relative to the axis of the arm whereby the apparatus can also be secured to the boney structure on laterally opposite sides of the portion of the boney structure to be harvested.

In another preferred feature of the first aspect of the present invention, the rigid arm has a locating screw threadably engaged in the arm and having a tip portion adapted to be located in a shallow hole drilled in the boney structure adjacent the operating axis, the locating screw having a shoulder spaced from the tip for engaging the surface of the boney structure whereby the position of the rigid arm and the operating axis is controlled. The depth of cut of the dowel cutter is controlled.

Preferably, the rigid arm is a straight elongated bar with its axis parallel to the operating axis and having a multiplicity of spaced apertures extending transverse to the operating axis for accommodating fixing pins for attaching the arm to the boney structure.

In a second aspect of the present invention, there is provided a method of harvesting a graft comprising plugs of boney structure interconnected by patellar tendon fibers using the apparatus according to the first aspect of the invention, the steps comprising:

surgically exposing the patella and its associated tendons;

securing the arm onto boney structure of the tibia by securing means;

advancing the dowel cutter along the boney structure so as to harvest a contiguous bone block containing the superficial fibres of the patellar tendon along its surface; and repeating the procedure to harvest the boney structure from the femoral end.

The above procedure produces a graft comprising plugs of boney structure interconnected by fibers of the patellar tendon.

In a third aspect of the present invention, there is provided a second apparatus for grafting plugs of boney structure into a tibia or femur, the apparatus comprising:

a fixing pin guide comprising (a) an elongated track from which a stem extends substantially at right angles, the stem being adapted to be inserted in a drilled canal in the end region of a bone; and (b) a sliding block having mounting means for slidably mounting the block on the elongated track for motion towards and away from the stem, the block having at least one bore extending substantially at right angles to the stem for receiving and guiding a fixing pin which is to be driven into the bone substantially at right angles to the canal therein, the stem acting as an abutment for preventing insertion of the fixing pin across the canal until the stem has been withdrawn and a plug of boney structure of corresponding configuration has been inserted in the canal.

Preferably the track has a recess extending therealong and accommodating a flange protruding from the mounting block, the recess extending through the track for accommodating two screw-threaded studs which protrude when in use through the recess and receive clamping screws whereby the mounting block can be adjusted to the desired position and clamped in position to facilitate driving of the fixing pin through the selected bore in the sliding block.

In a fourth aspect of the present invention there is provided a method of performing a cruciate ligament graft using apparatus according to a second aspect of the invention, the steps comprising:

taking a graft comprising plugs of boney structure interconnected by fibers of the patellar tendon;

drilling a canal through the femur and inserting the stem of the fixing pin guide into the canal;

mounting the sliding block on the track with its mounting means and adjusting the position of the sliding block so an end thereof is adjacent the femur, guiding a fixing pin through the selected bore and sliding block and driving it through the femur to come into abutment with stem located in the drilled canal in the femur and removing the fixing pin guide by withdrawing the stem from the canal and withdrawing the mounting block from over the pin;

inserting one of the plugs of boney structure into the canal and advancing the previously inserted fixing pin across the plug of boney structure; and repeating the procedure to secure the other boney plug in the tibia and to secure it with a further fixing pin.

It is preferable that the graft comprising the plugs of boney structure is harvested using the apparatus according to the first aspect of the invention.

The fixing pin is preferably a Steinmann pin, such as a 3/32nd Steinmann pin. (2.4 mm diameter)

BRIEF DESCRIPTION OF THE DRAWINGS

The invention will now be further described by way of example with reference to the accompanying drawings in which:

FIG. 5 is a front elevation of a mounting track of a pin guide unit and for use with the sliding block of FIGS. 7 and 8;

FIG. 6 is an underside view of the pin guide shown in FIG. 5;

FIG. 7 is a front view of a sliding block used on the mounting track of FIGS. 4 and 5 and for guiding Steinmann pins; and FIG. 8 is a side view of the sliding block shown in FIG. 7.

DETAILED DESCRIPTION OF THE DRAWINGS

Figure 1:
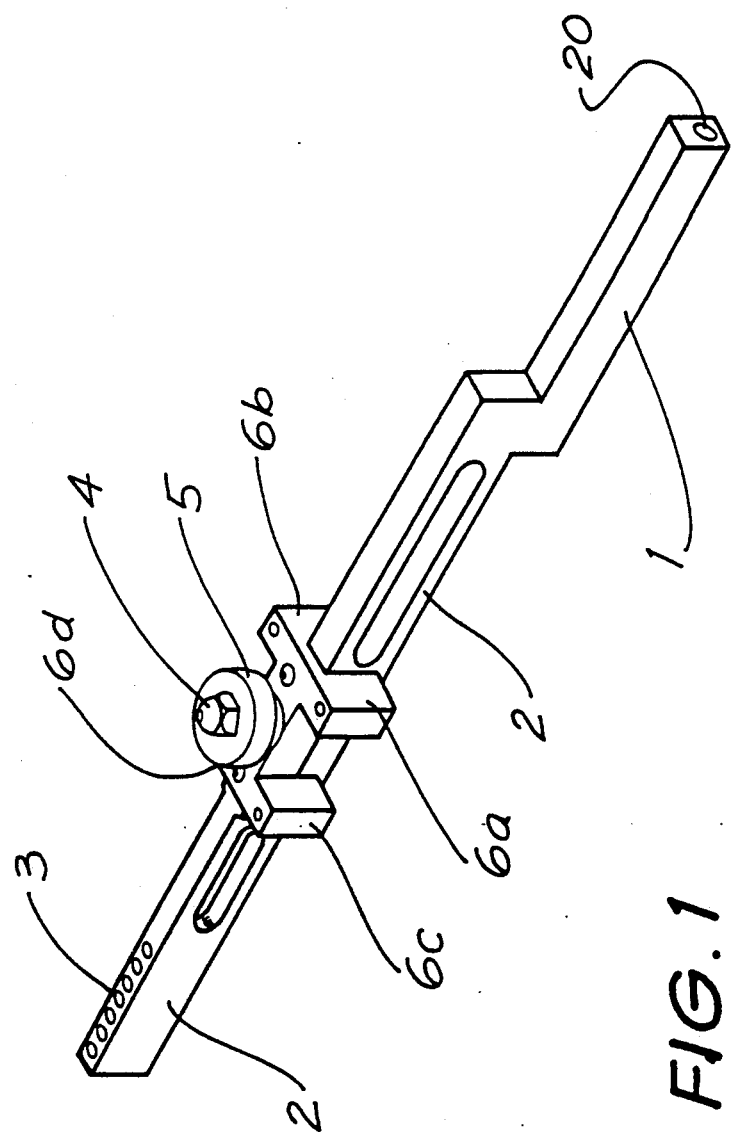
FIG. 1 shows apparatus embodying the invention for harvesting plugs of boney structure.
Figure 3:
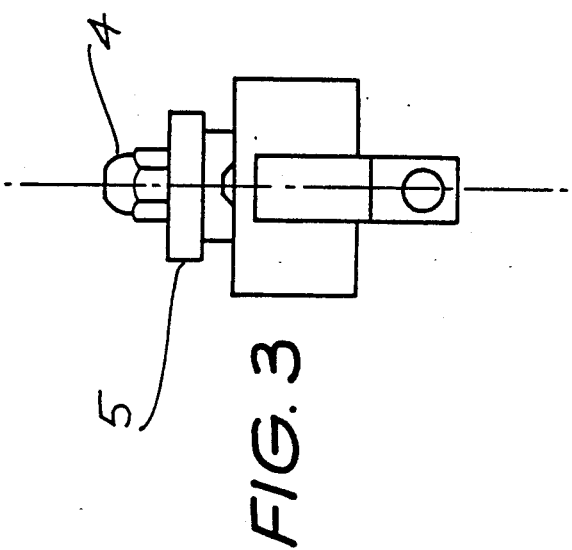
FIG. 3 shows a locating screw which threadably engages in the rigid arm of the apparatus of FIG. 1.

The apparatus shown in FIGS. 1 to 4 is used for harvesting plugs of boney structure and strip of tendon. The apparatus is made of surgical steel and comprises a dowel cutter support guide 1, and an elongated arm 2, which is offset and has a remote end portion having a series of transverse bores 3 providing alternative locations for accomodating securing pins. The central region of the arm 2 has two pairs of laterally extending shoulders 6a, 6b, 6c, 6d each having a bore 6c for accommodating a securing pin.

Midway between the pairs of shoulders the arm 2 has a threaded bore 4a accommodating a locating screw 4 which has an enlarged head 5 with a knurled periphery and, at the opposite end, a pointed tip 11 extending from a flat annular shoulder 10.

Figure 2:
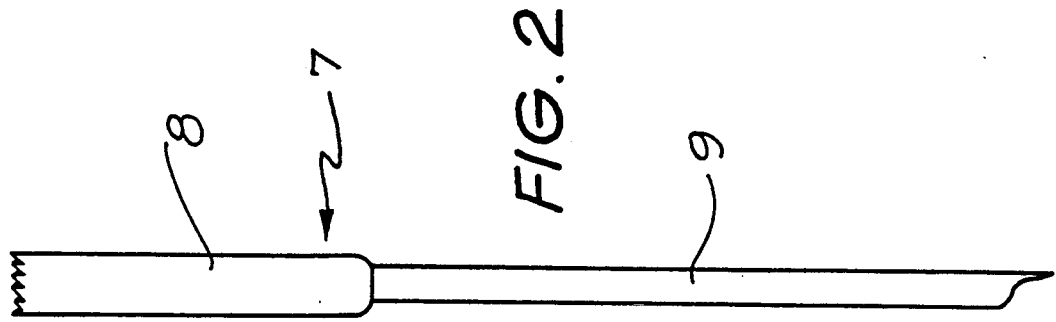
FIG. 2 shows a dowel cutter which can be rotatably mounted in the mounting means of the apparatus shown in FIG. 1.
Figure 4:
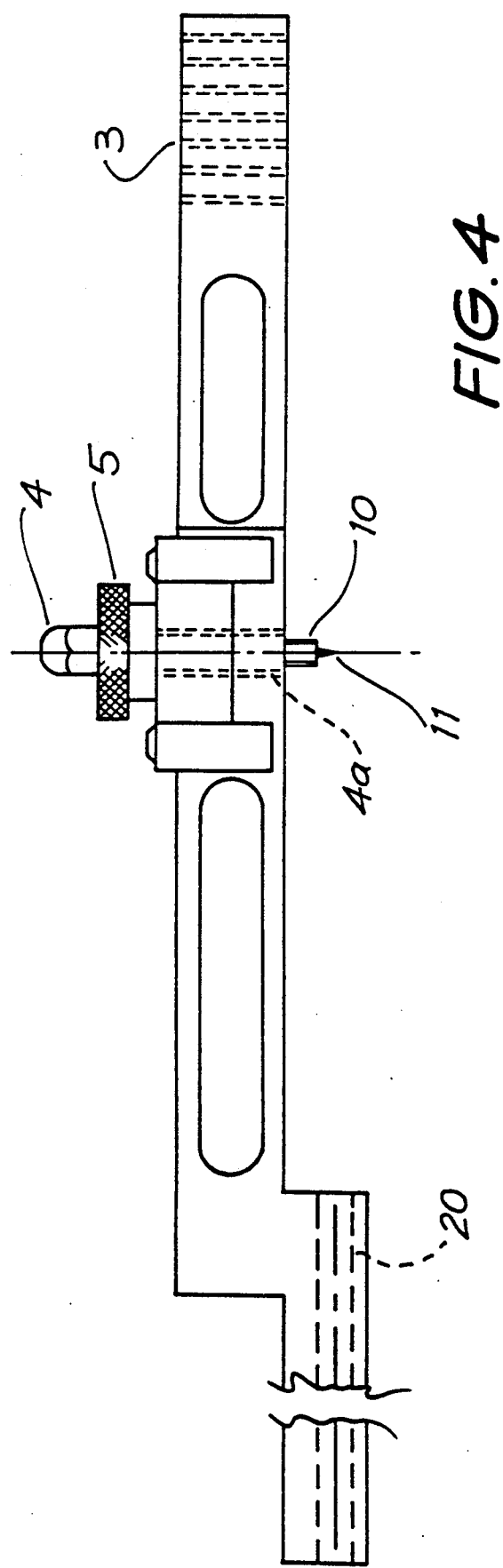
FIG. 4 is a rear view of the apparatus shown in FIG. 1.

The dowel cutter support guide 1 has an elongated bore 20 extending along an operating axis for rotably mounting the shaft 9 of the dowel cutter 7 shown in FIG. 2. The dowel cutter has a tubular cutting head 8. In use, the stem 9 is located in the bore of the dowel cutter support guide 1 and the stem 9 is rotated by a power tool and slides forwardly as a dowel is cut.

The patella and its associated tendons are surgically exposed and a wedge of tibia is removed using a chisel and hammer to provide a square edge. A small shallow hole is drilled into the tibial tubercle to provide a recess for the tip 11 of the locating screw 4, the shoulder 10 of the locating screw engaging on the surface of the tibia.

The elongated arm 2 of the apparatus shown in FIG. 1 is secured to the patella using Steinmann pins drilled through the transverse bores 3, and through two of the bores 6c on the laterally extending shoulders 6a and 6b. The tubular head 8 of the dowel cutter 7 is advanced along the boney structure disposed thereunder so as to harvest a contiguous bone block comprising a section of the tibia and the superficial fibers of the patellar tendon.

Once a cutting track has been established in the bone block, the locating screw 4 is retracted and the dowel cutter 7 is advanced further. This procedure will produce a tibial bone plug. The apparatus 2 is released from the boney structure by removing the Steinmann pins.

The apparatus is then relocated first by drilling a hole in the highest point of the patella in which to locate the tip 11 of the locating screw 4 with the shoulder 10 of the locating screw 4 engaging on the surface of the patella. The elongated arm 2 is secured to the tibia using Steinmann pins inserted through selected ones the transverse bores 3. Two further Steinmann pins are drilled through the auxiliary securing means 6 to secure the arm to the patella.

The harvesting procedure as described above is now repeated with the dowel, cutter 7 advancing downwardly towards the tibia whereby to harvest boney structure from the patella. The plug of boney structure which is harvested by this procedure contains the superficial fibers of the patellar tendon which may act as a graft.

The patella is then dislocated laterally and remnants of the anterior cruciate excised, removing any osteophytes which may have built up.

A guide wire is drilled just superior and posterior to the site of the anatomical attachment of the anterior cruciate ligament to the femur. The guide wire exits on the lateral surface of the femur just anterior to the lateral supracondylar ridge. The guide wire is overdrilled using a 9.5 mm canulated drill. A similar drill hole is placed in the tibia. The guide wire is placed just anterior and medial to the true anatomical centre of attachment. Once the guide wire has been overdrilled the edge of the canal will move to the true center of attachment of the anterior cruciate ligament.

The exit hole in the femur is exposed with blunt dissection underneath the vastus lateralis muscle.

Fixation of the harvested boney plugs uses the apparatus of FIGS. 5 to 8. This apparatus comprises a rigid unit shown in FIG. 5 comprising an elongated track 12 and a circular cross-section lateral stem 13 extending from one end for insertion to the canal drilled in the bone which is to receive the boney plug. The track is adapted to mount a sliding guide block shown in FIGS. 7 and 8 and which is provided for guiding accurately a Steinmann pin when it is driven laterally into the bone to intersect with the canal drilled in the bone. The components are preferably of stainless steel. The track 12 has an elongated slot 12a extending along the track, the cross-sectional shape of the track being basically of circular cross-section with a flat rear face 12b to provide an abutment base for knurled securing screws which, as described below, secure the mounting block in the desired operating position. The track also has a tapped bore 12c in its end region. At the opposite end the stem 13 is fixed e.g. by welding. The free end of the stem has a shallow taper 13a to facilitate insertion into the canal drilled into the bone and in its region near the track 12, the stem has a transverse bore 13b which, as shown in FIG. 6, extends at an angle of approximately 60° to the axis of the track.

As shown in FIGS. 7 and 8, the guide block 15 has a body portion 15a having a series of 3 bores 17 extending therethrough and any one of which is selected for accommodating the fixing pin, and along its upper edge (as illustrated) there is a flange 15b for being accommodated in the recess 12a of the track. Two screw threaded studs 16 project from flange 15b and the length of these studs is such that they will project through recess 12a and knurled fixing screws (not shown) are then used to clamp the mounting block to the selected position along the track.

In use the guide block 15a is secured to the track using the knurled nuts and the stem 1 inserted through the drilled canal in the bone. The knurled nuts are slackened and the mounting block slid along to be adjacent the bone. A Steinmann pin is inserted through the selected bore 17 and driven with a power tool through the bone until it abuts the stem 13. The apparatus in FIGS. 6 to 8 is then withdrawn conveniently by slackening off and removing the knurled nuts used on the stud 16 thereby permitting a lateral withdrawal of the stem and track and the mounting block is slid off the Steinmann pin.

Similarly the apparatus in FIGS. 5 to 8 is used to prepare a corresponding canal in the tibia with a Steinmann pin driven laterally into the bone with its tip at the sidewall of the canal.

A loop of wire is passed into the femoral tunnel into the joint. Sutures are passed through each boney block so that the graft can be pulled into the tunnel and to control the tension of the graft.

The lateral cut to complete the ressection of tendon graft is made. The fat pad is dissected away from the back of the remaining patellar tendon to give greater length and mobility of the pedicle. The graft is then introduced into the joint through a vertical incision in the infrapatellar fat pad.

The patellar is dislocated laterally and the graft is manoeuvered into the joint. The graft is inverted and turned 180° along its long axis so that the original anterior surface will now be facing backwards so that the vascular pedicle is appropriately directed.

The tibial plug of boney structure is then inserted into the femoral canal with traction being applied to the thread attached to it.

The wire loop is threaded into the tibial tunnel. A suture is looped through the pull-through wire and the patellar plug is inserted into the canal and the graft adjusted into position using two threads.

The upper end of the graft is then fixed in the canal by advancing the previously inserted Steinmann pin across the graft with the pin being punched flush to the bone.

Using wire loops and by pulling the graft, the desired tension is set. The tibia is pushed backwards to reduce the tibia on the femur during this step of the procedure. The boney plug is then fixed in position with the Steinmann pin which is finished and punched flush with the bone.

The procedure is completed by closing the wound in layers.

I claim:

1. A method of cruciate ligament replacement comprising harvesting a graft comprising first and second plugs of boney structure interconnected by superficial fibers of a patellar tendon, the method comprising:

surgically exposing the patella and its associated tendons;

advancing a dowel cutter along boney structure of the tibia so as to harvest the first plug of boney structure comprising a contiguous bone block containing the superficial fibers of the patellar tendon along its surface; and repeating the procedure to harvest the second plug of boney structure comprising boney structure from the patella;

installing the graft by drilling a canal through the femur and inserting a stem of a fixing pin guide into the canal;

driving a fixing pin through the femur to come into abutment with the stem inserted in the drilled canal in the femur and removing the fixing pin guide by withdrawing the stem from the canal;

inserting one of the plugs of boney structure into the canal and advancing the previously inserted fixing pin across the inserted plug of boney structure to secure it; and repeating the procedure to insert the other boney plug in the tibia and to secure it with a further fixing pin.

2. A method as claimed in claim 1, said method further comprising securing a guide structure for the dowel cutter to the tibia and to the patella for controlling the axis along which the dowel cutter moves, and guiding the dowel cutter through the guide structure for harvesting said first plug, said method further comprising, prior to harvesting said second plug, relocating and securing the guide structure to the patella and the tibia for guiding movement of the dowel cutter during harvesting the second plug, and engaging the dowel cutter with the guide during harvesting of the second plug.

3. A method as claimed in claim 2, said method further comprising adjusting a locating screw threadably engaged in a rigid arm of the guide structure such that a tip of the locating screw engages the tibia during harvesting the first plug and engages the patella during harvesting of the second plug, the adjustment being carried out to control the position of the guide structure whereby the axis along which the dowel cutter is guided to move is defined.

4. A method as claimed in claim 2, wherein prior to harvesting the first plug the method comprises pinning the guide structure to the tibia at locations on laterally opposite sides of the boney structure to be harvested and pinning a distal portion of the guide structure to the patella.

* * * * *